US00PP16242P2

(12) United States Plant Patent
Schmulling

(10) Patent No.: US PP16,242 P2
(45) Date of Patent: Feb. 7, 2006

(54) *OSTEOSPERMUM* PLANT NAMED 'BALSERLAV'

(50) Latin Name: *Osteospermum hybrida*
Varietal Denomination: Balserlav

(75) Inventor: Markus Schmulling, Billerbeck (DE)

(73) Assignee: Ball Horticultural Company, West Chicago, IL (US)

( * ) Notice: Subject to any disclaimer, the term of this patent is extended or adjusted under 35 U.S.C. 154(b) by 93 days.

(21) Appl. No.: 11/023,224

(22) Filed: Dec. 27, 2004

(51) Int. Cl.
*A01H 5/00* (2006.01)

(52) U.S. Cl. ..... Plt./360
(58) Field of Classification Search ..... Plt./360
See application file for complete search history.

*Primary Examiner*—Kent Bell
(74) *Attorney, Agent, or Firm*—Wood, Phillips, Katz, Clark & Mortimer

(57) ABSTRACT

A new and distinct cultivar of *Osteospermum* plant named 'Balserlav' characterized by its single inflorescence form with lavender-colored ray florets, violet-blue-colored disc florets, dark green-colored foliage, freely branching character, and compact, upright, and mounded growth habit.

1 Drawing Sheet

Latin name of the genus and species of plant claimed: *Osteospermum hybrida.*
Variety denomination: 'Balserlav'.

BACKGROUND OF THE INVENTION

The present invention relates to a new and distinct cultivar of *Osteospermum* plant botanically known as *Osteospermum hybrida* and hereinafter referred to by the cultivar name 'Balserlav'.

The new *Osteospermum* originated in a controlled breeding program in Billerbeck, Germany, during August 1999. The objective of the breeding program was the development of *Osteospermum* cultivars that are freely branching, have a compact and upright growth habit, are freely flowering, and have unique inflorescence coloration.

The female parent of the new cultivar was the proprietary *Osteospermum hybrida* breeding selection designated 09-19-98, not patented, characterized by its white-colored ray florets, yellow-colored disc florets, and vigorous growth habit. The male parent of the new cultivar was the proprietary *Osteospermum hybrida* breeding selection 17-44-98, not patented. Seed from the above stated cross-pollination was germinated and grown to maturity. A single flowering plant within the progeny was discovered and selected by the inventor during April 2000 in a controlled environment at Billerbeck, Germany.

Asexual reproduction of the new cultivar by terminal stem cuttings taken since April 2000 at West Chicago, Ill. has demonstrated that the new cultivar reproduces true to type, with all the characteristics as herein described, firmly fixed and retained through successive generations of such asexual propagation.

SUMMARY OF THE INVENTION

The following characteristics of the new cultivar have been repeatedly observed and can be used to distinguish 'Balserlav' as a new and distinct cultivar of *Osteospermum* plant:

1. Single inflorescence form with lavender-colored ray florets and violet-blue-colored disc florets.
2. Dark green-colored foliage.

3. Freely branching character.
4. Compact, upright, and mounded growth habit.

Plants of the new cultivar differ from plants of the female parent primarily in inflorescence color and growth habit and from plants of the male parent primarily in leaf size.

Plants of the new cultivar are most similar to the cultivar Aksinto, U.S. Plant Pat. No. 12,261. However, in side-by-side comparisons, plants of the new cultivar differed from plants of 'Askinto' in the following characteristics:

1. Plants of the new cultivar are taller and less spreading than plants of 'Aksinto'.
2. Plants of the new cultivar have larger inflorescences than plants of 'Aksinto'.

BRIEF DESCRIPTION OF THE PHOTOGRAPHS

The accompanying photographs show, as nearly true as it is reasonably possible to make the same in color illustrations of this type, typical inflorescence and foliage characteristics of the new cultivar. Colors in the photographs differ slightly from the color values cited in the detailed description, which accurately describe the colors of 'Balserlav'. The plants were grown in 10 cm pots for 18 weeks in the field at West Chicago, Ill.

DETAILED BOTANICAL DESCRIPTION

Figure 1:
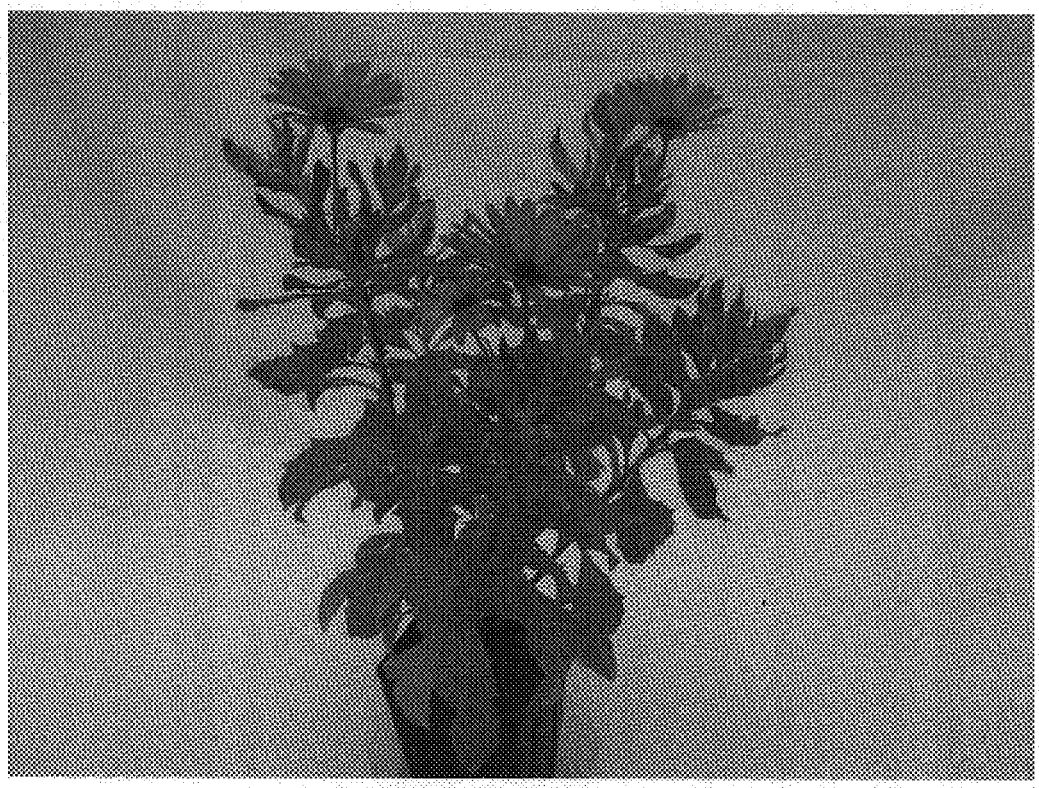
FIG. 1 illustrates a side view of the overall growth and flowering habit of 'Balserlav'.
Figure 2:
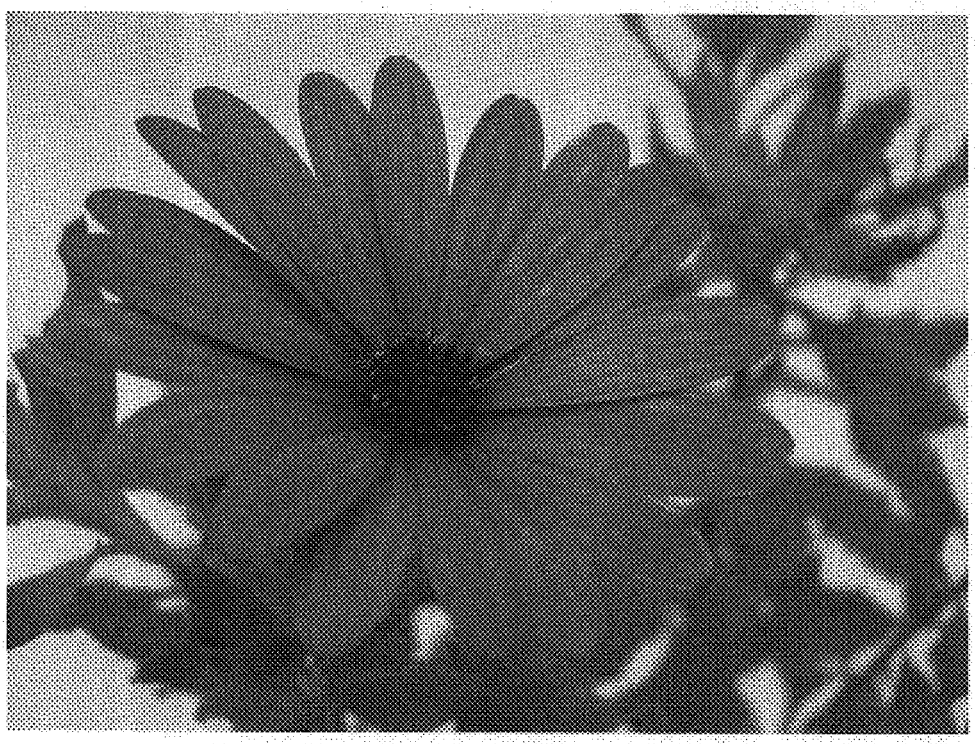
FIG. 2 illustrates a close-up view of an individual inflorescence of 'Balserlav'.

The new cultivar has not been observed under all possible environmental conditions to date. Accordingly, it is possible that the phenotype may vary somewhat with variations in the environment, such as temperature, light intensity, and day length without, however, any variance in genotype.

The chart used in the identification of colors described herein is The R.H.S. Colour Chart of The Royal Horticultural Society, London, England, 2001 edition, except where color terms of ordinary significance are used. The color values were determined on Sep. 24, 2004 between 1:00 and 3:00 p.m. under natural light conditions.

The following descriptions and measurements describe plants produced from cuttings taken from stock plants and grown at West Chicago, Ill. in a double polycarbonate covered greenhouse under conditions comparable to those used in commercial practice. The plants were grown in 10 cm pots for 18 weeks while utilizing a soilless growth medium. Greenhouse temperatures were maintained at approximately 65°–78° F. (18°–25° C.) during the day and approximately 50°–60° F. (10°–15° C.) during the night. Greenhouse light levels were maintained at 6,000 to 9,000 footcandles during the day.

Botanical classification: *Osteospermum ecklonis* cultivar Balserlav.

Parentage:

*Female parent*.—Proprietary breeding selection 09-19-98, not patented.

*Male parent*.—Proprietary breeding selection 17-44-98, not patented.

Propagation:

*Type cutting*.—Terminal stem.

*Time to initiate roots*.—Approximately 9 to 12 days.

*Time to produce a rooted cutting*.—Approximately 21–28 days.

*Root description*.—Fine, fibrous.

*Rooting habit*.—Freely branching.

Plant description:

*Crop time*.—Approximately 10–13 weeks from rooted cutting.

*Growth habit*.—Compact. Freely branching. One or two pinches improves basal branching.

*Form*.—Upright, mounded.

*Size*.—Height — Approximately 38.4 cm from soil level to top of plant plane. Width to outer inflorescences (area of spread): Approximately 28.2 cm.

*Branch*.—Quantity per plant: Approximately 4 main branches. Strength: Strong. Aspect: Erect. Length from soil level to base of peduncle: Approximately 27.2 cm. Diameter at base: Approximately 5.5 mm. Texture: Glabrous. Color: 144B. Internode length at middle of branch: Approximately 8.3 mm.

*Foliage*.—Quantity per branch: Approximately 33. Type: Simple. Fragrance: Faint. Arrangement: Alternate. Aspect: At an acute angle to the stem. Shape: Elliptic, pinnatified. Apex: Acute. Base: Decurrent. Margin: Widely dentate. Venation pattern: Pinnate. Length: Approximately 6.5 cm. Width: Approximately 2.4 cm. Texture: Upper and lower surface: Papillate. Color of upper surface of mature foliage: Darker than 146A with venation of 145B. Color of lower surface of mature foliage: 146B with venation of 145B.

Flowering description:

*Time to first flower*.—Approximately 10–13 weeks from planting of rooted cutting.

*Flowering habit*.—Freely flowering under outdoor growing conditions with substantially continuous blooming from spring through autumn and year round in greenhouse environment.

*Flower arrangement*.—Solitary, terminal.

*Lastingness of inflorescence*.—Approximately 4–6 days.

Inflorescence description:

*Appearance*.—Type: Composite, persistent. Shape: Round. Aspect: Slightly cupped, facing upward or outward. Disc and ray florets develop acropetally on a capitulum. Fragrance: None.

*Quantity of inflorescences and buds per lateral branch*.—Approximately 1 inflorescence and 4 buds.

*Size*.—Diameter: Approximately 5.8 cm. Depth: Approximately 1.7 cm.

*Bud*.—Rate of opening: Generally takes from 3–6 days for buds to progress from first color to fully open inflorescences. Shape: Elliptic. Depth: Approximately 1.5 cm. Diameter: Approximately 9.3 mm. Color: 144B.

*Ray florets*.—Quantity per inflorescence: Approximately 21. Arrangement: Overlapping. Aspect: Flat to slightly concave. Shape: Linear. Apex: Emarginate with three tips. Base: Attentuate and fused to form tube. Margin: Entire. Length: Approximately 3.2 cm. Width at widest point: Approximately 7.2 mm. Testure: Glabrous and ribbed. Color of upper and lower surface of fully open ray floret: N74C with ribs of N87B.

*Disc*.—Diameter: Approximately 9 mm. Depth: Approximately 1 cm.

*Receptacle*.—Diameter: Approximately 3 mm. Depth: Approximately 2 mm. Color: 154D.

*Disc florets*.—Quantity per inflorescence: Approximately 70. Shape: Tubular with five lobes each having an acute apex. Margin: Entire. Length: Approximately 8 mm. Diameter at apex: Approximately 3 mm. Diameter at base: Approximately 1 mm. Texture: Glabrous. Color of immature florets: N92B. Color of mature florets: 96B.

*Phyllaries*.—Quantity per inflorescence: Approximately 20. Arrangement: Imbricate, arranged in several rows. Shape: Ovate. Apex: Acute. Base: Truncate. Margin: Entire. Length: Approximately 1.2 cm. Width: Approximately 1.9 mm. Texture of center of outer/lower surface: Rough. Texture of center of inner/upper surface: Glabrous. Color of center of outer/lower surface: Closest to 144B. Color of center of inner/upper surface: Closest to 144C. Texture of margins: Papery. Color of margins: 157B, transparent.

*Peduncle*.—Strength: Strong. Aspect: At an acute angle to the stem. Length: Approximately 8.6 cm. Diameter: Approximately 1.3 mm. Texture: Rough. Color: 144A.

*Reproductive organs*.—Androecium: Present on disc florets only. Stamen quantity: 4. Anther shape: Linear. Anther length: Approximately 2 mm. Anther color: 93A. Amount of pollen: Abundant. Pollen color: 14A. Gynoecium: Present on ray and disc florets. There is one pistil per floret. Pistil length: Approximately 6.4 mm. Stigma shape: Two parted. Stigma length: Approximately 1.3 mm. Stigma color: 79A. Style length: Approximately 3.3 mm. Style color: Lighter than N82C. Ovary size: Approximately 1.6 mm. Ovary color: 145C.

Seed and fruit production: Neither seed nor fruit production has been observed.

Disease and pest resistance: Resistance to pathogens and pests common to *Osteospermum* has not been observed.

What is claimed is:

1. A new and distinct cultivar of *Osteospermum* plant named 'Balserlav', substantially as herein shown and described.

* * * * *

UNITED STATES PATENT AND TRADEMARK OFFICE

CERTIFICATE OF CORRECTION

PATENT NO. : PP 16,242 P2
APPLICATION NO. : 11/023224
DATED : February 7, 2006
INVENTOR(S) : Markus Schmulling It is certified that error appears in the above-identified patent and that said Letters Patent is hereby corrected as shown below:

On the cover page under (73) Assignee, please change Ball Horticultural Company, West Chicago, IL (US) to F. A. Wilhelm Schmulling, Billerbeck, Germany.

Signed and Sealed this

Tenth Day of April, 2007

JON W. DUDAS
*Director of the United States Patent and Trademark Office*